United States Patent [19]

Henrick

[11] 4,235,777

[45] Nov. 25, 1980

[54] BENZYLPYRROLYLMETHYL ESTERS OF 3-(1,2-DIBROMO-2,2-DICHLOROETHYL)-2,2-DIMETHYLCYCLOPROPANECARBOXYLIC ACID

[75] Inventor: Clive A. Henrick, Palo Alto, Calif.

[73] Assignee: Zoecon Corporation, Palo Alto, Calif.

[21] Appl. No.: 95,283

[22] Filed: Nov. 19, 1979

[51] Int. Cl.$^3$ ............... C07D 207/33; C07D 207/325; C07D 207/333; A01N 43/36
[52] U.S. Cl. .............................. 260/326.43; 424/274
[58] Field of Search .................................. 260/326.43

[56] References Cited

U.S. PATENT DOCUMENTS

| 3,426,037 | 2/1969 | Biel et al. | 260/326.43 |
| 3,428,651 | 2/1969 | Kato et al. | 260/326.43 |

Primary Examiner—Donald G. Daus
Assistant Examiner—M. C. Eakin
Attorney, Agent, or Firm—Donald W. Erickson

[57] ABSTRACT

Benzylpyrrolylmethyl esters of 3-(1,2-dibromo-2,2-dichloroethyl)-2,2-dimethylcyclopropanecarboxylic acid, synthesis thereof and the use of said esters for the control of pests.

8 Claims, No Drawings

BENZYLPYRROLYLMETHYL ESTERS OF 3-(1,2-DIBROMO-2,2-DICHLOROETHYL)-2,2-DIMETHYLCYCLOPROPANECARBOXYLIC ACID

This invention relates to novel esters of 3-(1,2-dibromo-2,2-dichloroethyl)-2,2-dimethylcyclopropanecarboxylic acid, the synthesis thereof and their use in the control of pests.

The esters of the present invention are represented by the following formula (A):

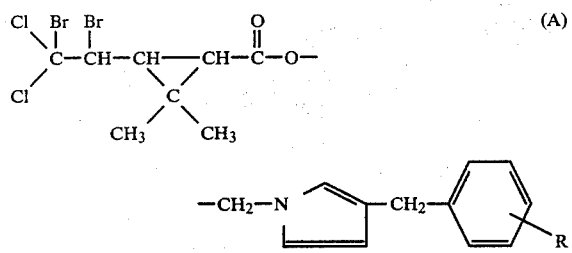

wherein R is hydrogen, fluoro, bromo, chloro, trifluoromethyl, methyl, methoxy, or methylthio.

The compounds of the present invention represented by formula (A) are useful agents for the control of pests such as insects and acarids.

The compounds of formula (A) can be synthesized as follows:

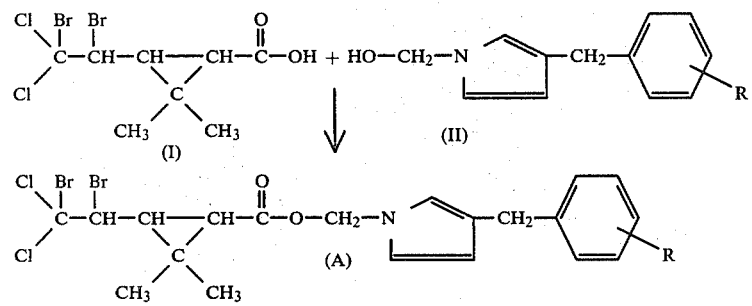

In the general practice of the above synthesis, an acid of formula I and an alcohol of formula II are reacted in an organic solvent such as methylene chloride in the presence of 4-N,N-dimethylaminopyridine and dicyclohexylcarbodiimide to form an ester of formula A.

The alcohols of formula II can be made as described by Ohsumi et al., Offenlegungsschrift No. 28 43 760.

The compounds of the present invention of formula (A) have one or more asymmetric carbon atoms. The present invention includes each of the optical isomers and racemic mixtures thereof. In the examples hereinafter, unless otherwise specified, the compound prepared in a racemic mixture.

The compounds of the present invention of formula A are useful pest control agents, particularly for the control of insects and acarids. In the use of the compounds of formula A for combating insects and acarids for the protection of agricultural crops, for example soybeans, cotton, alfalfa, etc., a compound of formula A, or mixtures thereof, together with a carrier is applied to the locus in a pesticidally effective amount. The carrier can be liquid or solid and include adjuvants such as wetting agents, dispersing agents and other surface active agents. The compounds of formula A can be used in formulations such as wettable powders, solutions, dusts, granules, emulsifiable concentrates, and the like. Suitable solid carriers include natural and synthetic silicates and clays, carbon or charcoal granules, natural and synthetic resins, waxes, and the like. Suitable liquid carriers include water, aromatic hydrocarbons, alcohols, vegetable and mineral oils, ketones, and the like. The amount of a compound of formula A in the formulation can vary widely, generally within the range of 0.01 percent to about 90.0 percent, by weight.

As shown hereinafter, the compounds of the present invention are effective on many different insects and on acarids. The compounds are effective control agents for insects such as mosquitoes, flies, aphids, weevils and acarids such as the spider mite and ticks. Depending upon the particular combination of the substituents of formula A herein, the compounds have a broad or relatively narrow spectrum of unusually high pesticidal activity on insects and acarids. Among the pests against which the compounds of the present invention are pesticidally effective are insects of the order Lepidoptera, Orthoptera, Heteroptera, Homoptera, Diptera, Coleoptera or Hymenoptera, and acarids of the order Acarina including mites of the family Tetranychidae and ticks such as Ornithodoros.

The compounds of the present invention can be used in combination with other pesticides such as the carbamates, phosphates and insect growth regulators, e.g., propoxur, carbaryl, naled, dichlorvos, phosmet, chlorpyrifos, acephate, diazinon, methoprene, kinoprene, hydroprene, cyhexatin, resmethrin, permethrin and fenvalerate.

The following examples are provided to illustrate the practice of the present invention. Temperature is given in degrees Centigrade.

EXAMPLE 1

To 0.97 g (4.7 mmol) of 3-(2,2-dichlorovinyl)-2,2-dimethylcyclopropanecarboxylic acid in 10 ml of carbon tetrachloride, heated to 50°, is very gradually added (over about 5 hours) 0.2 ml (6.0 mmol) of bromine in 2 ml carbon tetrachloride. During the addition, the reaction mixture is heated at 50° and stirred under nitrogen. The mixture is heated at 50° for one more hour, then cooled to room temperature and stirred for 4 hours. The solvent is evaporated and the resulting oil is put under high vacuum overnight, yielding 3-(1,2-dibromo-2,2-dichloroethyl)-2,2-dimethylcyclopropanecarboxylic acid.

To a mixture of 0.63 g (1.71 mmol) of 3-(1,2-dibromo-2,2-dichlorethyl)-2,2-dimethylcyclopropanecarboxylic acid, 0.32 g (1.71 mmol) of (3-benzyl-1-pyrrolyl)methanol and 0.01 g (0.08 mmol) of 4-dimethylaminopyridine in 10 ml of anhydrous methylene chloride at 5° and under nitrogen is added 0.35 g (1.71 mmol) of dicyclohexylcarbodiimide, with stirring. After 0.25 hour the slurry is warmed to room temperature and is stirred for 1 hour longer. The solid by-product is removed by filtration and the methylene chloride is evaporated off to give the crude product, which is taken up into 3 ml methylene chloride and filtered to remove any remaining by-product. The filtrate is diluted with ether, and the organic layer is washed with saturated sodium bicarbonate, with water until neutral and with brine, and then dried over calcium sulfate. Filtration and evaporation give the desired isomers, which are separated by preparative thin layer chromatography on silica gel developing with 15% ether/hexane, giving the cis and the trans isomers of (3-benzyl-1-pyrrolyl)methyl 3-(1,2-dibromo-2,2-dichloroethyl)-2,2-dimethylcyclopropanecarboxylate.

EXAMPLE 2

Following the procedure of Example 1, 3-(1,2-dibromo-2,2-dichloroethyl)-2,2-dimethylcyclopropanecarboxylic acid is reacted with [3-(4-fluorobenzyl)-1-pyrrolyl]methanol to give the final product [3-(4-fluorobenzyl)-1-pyrrolyl]methyl 3-(1,2-dibromo-2,2-dichloroethyl)-2,2-dimethylcyclopropanecarboxylate.

In like manner, 3-(1,2-dibromo-2,2-dichloroethyl)-2,2-dimethylcyclopropanecarboxylic acid is reacted with each of the alcohols in column I to give the resulting ester in column II.

I

[3-(3-fluorobenzyl)-1-pyrrolyl]methanol
[3-(3-methylbenzyl)-1-pyrrolyl]methanol
[3-(4-methoxybenzyl)-1-pyrrolyl]methanol
[3-(3-chlorobenzyl)-1-pyrrolyl]methanol
[3-(4-trifluoromethylbenzyl)-1-pyrrolyl]methanol

II

[3-(3-fluorobenzyl)-1-pyrrolyl]methyl 3-(1,2-dibromo-2,2-dichloroethyl)-2,2-dimethylcyclopropanecarboxylate
[3-(3-methylbenzyl)-1-pyrrolyl]methyl 3-(1,2-dibromo-2,2-dichloroethyl)-2,2-dimethylcyclopropanecarboxylate
[3-(4-methoxybenzyl)-1-pyrrolyl]methyl 3-(1,2-dibromo-2,2dichloroethyl)-2,2-dimethylcyclopropanecarboxylate
[3-(3-chlorobenzyl)-1-pyrrolyl]methyl 3-(1,2-dibromo-2,2-dichloroethyl)-2,2-dimethylcyclopropanecarboxylate
[3-(4-trifluoromethylbenzyl)-1-pyrrolyl]methyl 3-(1,2-dibromo-2,2-dichloroethyl)-2,2-dimethylcyclopropanecarboxylate Two groups of 10 each of 0-24 hour III instar *Heliothis virescens* larvae were treated with 1 µl of the compound (3-benzyl-1-pyrrolyl)methyl cis-3-(1,2-dibromo-2,2-dichloroethyl)-2,2-dimethylcyclopropanecarboxylate in acetone at three different concentrations by applications to the dorsum of the thorax. Two groups of 10 each are treated identically with 1 µl acetone as controls. Larvae are held individually in 30 ml plastic cups provided with artificial medium for 72 hours at 25° and 16 hr photoperiod. After 72 hours the number of dead is calculated as a percentage of the total number originally treated and then corrected for any mortality in the control groups using Abbott's formula. The $LD_{50}$ of the compound was less than 0.05%.

Twenty 0-24 hour III instar *Musca domestica* L. larvae are treated with 1 µl of either the compound (3-benzyl-1-pyrrolyl)methyl cis-3-(1,2-dibromo-2,2-dichloroethyl)-2,2dimethylcyclopropanecarboxylate or the compound (3-benzyl-1-pyrrolyl)-methyl trans-3-(1,2-dibromo-2,2-dichloroethyl)-2,2dimethylcyclopropanecarboxylate in acetone at three different concentrations by application to the posterior of larva. A group of twenty larvae are treated identically with 1 µl of acetone as controls. The larvae are held in an assay container for 7 days at 27° and 16 hr photoperiod. The effect is stated as the number which die as larvae or do not emerge from pupation calculated as a percentage of the total, corrected for any control mortality using Abbott's formula. Each of the above compounds gave an $LD_{50}$ of less than 0.5%.

What is claimed is:

1. A compound of the formula (A):

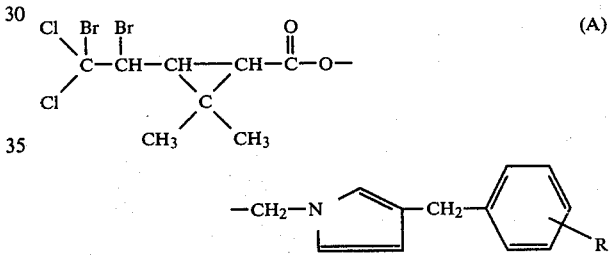

wherein R is hydrogen, fluoro, bromo, chloro, trifluoromethyl, methyl, methoxy or methylthio.

2. The compound according to claim 1 wherein R is hydrogen.

3. The compound according to claim 1 wherein R is in the meta position.

4. The compound according to claim 3 wherein R is fluoro.

5. The compound according to claim 1 wherein R is in the para position.

6. The compound according to claim 5 wherein R is fluoro.

7. The cis isomer of the compound according to claim 2.

8. The trans isomer of the compound according to claim 2.